United States Patent [19]

Gerbellot-Barrillon

[11] Patent Number: 4,509,919
[45] Date of Patent: Apr. 9, 1985

[54] ARTICULATOR FOR THE DENTAL ART

[75] Inventor: Pierre Gerbellot-Barrillon, Cluses, France

[73] Assignee: Fabrications Automatiques Gerbelot, Cluses, France

[21] Appl. No.: 569,768

[22] Filed: Jan. 10, 1984

[30] Foreign Application Priority Data

Jan. 12, 1983 [FR] France .................. 83 00793

[51] Int. Cl.³ .............................. A61C 11/00
[52] U.S. Cl. ..................................... 433/57
[58] Field of Search ..................... 433/56, 57

[56] References Cited

U.S. PATENT DOCUMENTS 4,290,754 9/1981 Edwardson ............... 433/57

Primary Examiner—Robert Peshock
Attorney, Agent, or Firm—Ratner & Prestia

[57] ABSTRACT

The invention provides an articulator for the dental art comprising an upper member articulated on condylar balls integral with a lower member, the balls being engaged in housings of the rear hub of the upper member. Two transverse rods, actuated by a control means engaging between the inner ends of the rods, are urged back towards the condylar balls and pass through the BENNETT wings. The control means comprises several different spacing zones for providing variable spacings between the rods which, either come into abutment against the balls to maintain the upper member in the centered position or they free the balls so as to allow an immediate lateral displacement.

13 Claims, 4 Drawing Figures

ARTICULATOR FOR THE DENTAL ART

BACKGROUND OF THE INVENTION

1. Field of the Invention

The present invention relates to articulators for the dental art, used for carrying out dental prosthesis and occlusal analysis work.

These apparatus, while serving as supports for lower and upper jaw moldings, allow the mandibular movements to be reproduced.

2. Description of the Prior Art

The articulators usually used comprise a lower platen whose front part supports an incisive table, and whose rear part comprises vertical legs supporting two condylar balls forming ball joints to which an upper member is hinged. The upper member comprises a rear hub having appropriate housings for housing the condylar balls and forming an articulation. A lower platen, integral with the hub, receives in its front part an incisive rod coming to bear on the incisive table for positioning the upper member with respect to the lower platen.

For reproducing the movements of the jaw, the housings of the hub are usually limited by a flat upper guide ramp slanting towards the front by an angle reproducing the condylar slope; a lateral outer ramp, or BENNETT's wing, open towards the front by an angle reproducing BENNETT's angle, limits the movement of the ball outwardly; a rear wall limits the movements of the ball rearwardly while allowing transverse movements. The lower and upper jaw moldings are fitted to the device by means of mounting plates fixed to the central part of the lower platen and of the upper platen.

French Pat. No. 2 431855 describes such an articulator in which provision is further made for making BENNETT's wings adjustable by lateral translation with respect to the housing of the hub; bringing the two BENNETT's wings closer together, in relation with a constant spacing of the condylar balls, provides a play which allows the movement called immediate lateral displacement, to be reproduced, that is to say a transverse translation of the upper member with respect to the lower member, the condylar balls remaining in contact with the rear wall, before reproducing a BENNETT movement by sliding of a ball against the corresponding BENNETT's wing.

In this document are also described means for selectively locking the hub in centered relation. By selective locking in centered relation is meant a function, according to which the user, after choosing an immediate lateral displacement of a given value, may instantaneously prevent the transverse translation momentarily so as to reproduce a pure centered rotational movement of the upper member with respect to the lower member, and may then instantaneously again allow the transverse translation without having to adjust its value a second time. The means described in this document comprise a rod integral with an intermediate cross piece of the lower member, and coming to bear selectively in a circular peripheral groove provided in the hub. The articulator described thus comprises means for allowing an immediate lateral displacement of the lower member and means for selectively obtaining locking thereof in centered relation.

However, such an arrangement leads to the construction of expensive articulators, for reproduction of the immediate lateral displacement movement requires the use of relatively complex housings. The number of precision machined parts is relatively high, which leads to a high cost. The intermediate cross-piece or the rod which is associated therewith prevents or considerably hinders access to the prothesis through the rear of the apparatus. The adjustments require the handling of several parts: BENNETT's wings for choosing the amplitude of translation, and the rod for locking or unlocking.

Patent NL-A-80 06043 describes an articulation in which the condylar balls are integral with the upper member and engage in housings integral with the lower member. The condylar balls have an adjustable spacing. For that, they are each mounted on half shafts sliding in the upper member, held apart by a spring and actuated by superimposed sliding plates. This device allows the immediate lateral displacement to be adjusted, but the pure centered rotation can only be obtained by moving the two sliding plates and thus losing the information about the preceding lateral displacement value. The device does not allow selective locking in centered relation.

The object of the present invention is in particular to overcome the drawbacks of the known devices by proposing an articulator allowing the immediate lateral displacement to be adjusted in simple way with selective locking in centered relation by operating a single member.

Another object of the present invention is to provide articulators whose centered relation blocking devices are particularly simple, easy and rapid to use, do not hinder access through the rear of the articulator and lead to using a minimum of precision machined parts.

Another object of the invention is to propose an articulator in which the amplitude of the immediate lateral displacement movement is chosen equal to a predetermined value, corresponding to the majority of cases met with in the usual human morphologies; the same articulator may further reproduce two immediate lateral displacement amplitudes, covering the majority of morphological cases for different ages.

Another object of the invention is to propose an articulator in which the centered relation locking device may be associated with a device for the immediate pinning of the upper member on the lower member and the immediate unpinning thereof without manipulating levers or other accessories. The articulator thus designed is very easy to use because the preset values of immediate lateral displacement, of BENNETT's angle and of condylar slope reduce considerably the settings required for using the apparatus.

The preset values thus defined, identical for all the apparatus of the same series, allow the user to use several articulators successively and equally well for working the same prosthesis.

SUMMARY OF THE INVENTION

To achieve these objects as well as others, the present invention provides, according to one of its features, for the housings in which the condylar balls are housed to be defined by an upper wall, BENNETT's wings, and a rear wall. The centered relation selective locking is provided by means of two rods sliding transversely in the hub, that is to say parallel to the axis of the hub. The rods are moveable between a close-up position in which they release the condylar balls, allowing immediate lateral displacement of the upper member because the spacing between the condylar balls is greater than the spacing between the BENNETT's wings, and a spaced apart position in which the rods bear without play against the condylar balls symmetrically with respect to the longitudinal median plane of the upper member. A control member ensures operation of the rods and holds them in one or other position. With this arrangement, locking and unlocking in centered relation may be achieved by operating a single control member, releasing or blocking the two condylar balls at the same time. The user may thus free one of his two hands.

According to another feature of the invention, the control member comprises a spacer, moveable perpendicularly to the axis of the rods by the user and insertable between the two inner ends of the rods so as to push them back outwardly by its bearing faces. The bearing faces comprise a reduced spacing zone for leaving the rods in the closer position when they are in abutment on this zone, and at least one larger spacing zone for then holding the rods in the spaced apart position. Thus a reliable and particularly inexpensive device is obtained.

According to another feature of the invention, the spacer is generally wedge shaped. With this arrangement, by progressive insertion of the spacer, the amplitude of the immediate lateral movement may be adjusted at will.

In another alternative, this spacer comprises a reduced and constant spacing zone, a second zone whose spacing is constant and greater by about 2.5 millimeters with respect to the first zone, and a third zone whose spacing is constant and greater by about 4 millimeters with respect to the first zone. The zones are joined together by wedge shaped surfaces joining up the ends of the rods progressively from one zone to the other. Thus pre-programming of the amplitude of the immediate lateral displacement movement is provided, the amplitude being 1.25 millimeters on each side or 2 millimeters, which covers in a simple way the majority of cases met with in anatomy.

According to another feature of the invention, the rods are urged by resilient means tending to draw them closer to one another. With this arrangement, associated more especially with the preceding arrangement in which the spacer comprises a succession of constant spacing steps or zones, automatic return of the rods towards the center can be obtained and at the same time braking of the spacer by friction of the ends of the rods on the steps.

In another embodiment, the outer ends of the rods are integral with BENNETT's wings which are themselves moveable in translation in a transverse direction. Thus the difference in spacing between BENNETT's wings and the condylar balls is adjusted directly, thus adjusting the immediate lateral displacement.

In another variant, BENNETT's wings have a fixed spacing less than the spacing between the condylar balls; the rods pass through a bore provided in the BENNET's wings so as to come into abutment, in the spaced apart position, against the BENNETT's wings. This arrangement leads to simpler and less expensive constructions.

In this embodiment there are further provided means for adjusting the spacing between the condylar balls, so as to allow the amplitude of the immediate lateral displacement to be modulated. These adjusting means further allow possible deformation of the lower members of the articulator, particularly a fall or a shock, to be compensated for so as to bring the condylar balls back into symmetrical positions with desired spacing. For that removeable centering blocks are provided adaptable respectively to the upper platen and to the lower platen of the articulator and able to be fitted one in the other so as to hold the upper member in the centered position. This arrangement, associated with the other means for providing predetermined adjustments, ensures the interchangeability of the apparatus.

BRIEF DESCRIPTION OF THE DRAWINGS

Other features and advantages of the present invention will be clear from the following description of particular embodiments, made with reference to the accompanying Figures in which.

DESCRIPTION OF THE PREFERRED EMBODIMENT

Figure 1:
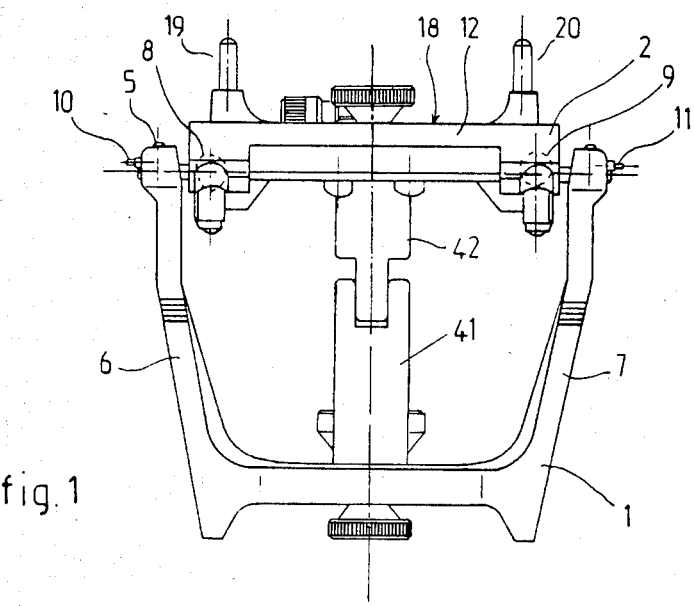
FIG. 1 shows a rear view of an articulator in accordance with the present invention.
Figure 2:
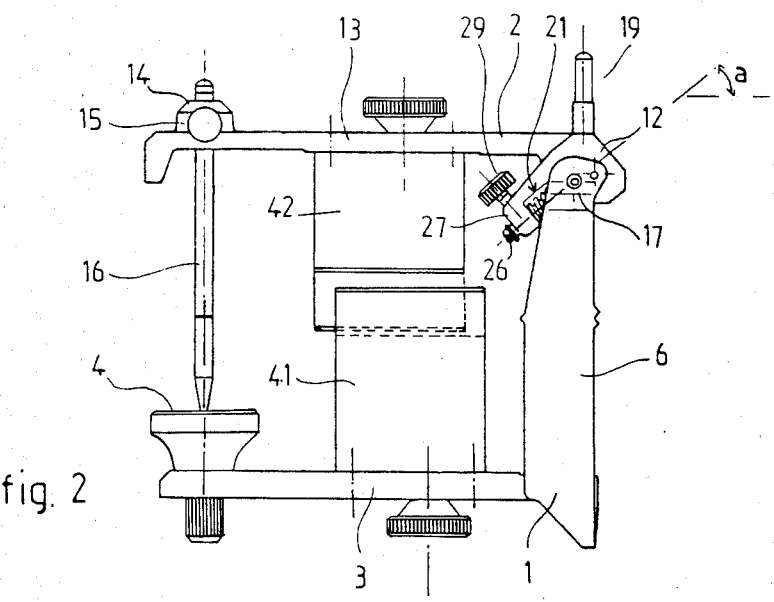
FIG. 2 shows a side view of the articulator of FIG. 1.

As shown in FIGS. 1 and 2, the articulator generally comprises a lower member 1 to which is hinged an upper member 2. The lower member 1 comprises a lower platen 3 whose front part supports an incisive table 4. The central part of platen 3 provides for fitting a lower mounting plate, not shown in the Figure. The rear part of platen 3 is joined to two vertical legs 6 and 7 whose upper zones each support a condylar ball respectively 8 and 9. The condylar balls are disposed opposite each other and project from the inner faces of the vertical legs 6 and 7. They are integral with the fixed shaft sliding in a corresponding bore 17 in the leg, in which bore the shafts are locked by locking screws 5.

To the outer part of the legs are fixed two pivoting shafts 10 and 11 which correspond to the auricular axis and allow adaptation of a facial arc.

The upper member 2 can be spit-mounted on the condylar balls 8 and 9 and, for that, comprises a hub 12 integral with the upper platen 13. The front part of platen 13 comprises a guide and locking device 14 comprising a barrel with a vertical axis and a transverse locking screw 15. An incisive rod 16 is introduced and locked in the barrel so as to bear on the incisive table 4 and hold the upper member in position.

The central part of the upper platen 13 comprises a positioning device on which is fitted an upper mounting plate not shown.

The hub 12 has on its upper face 18 two stabilizing feet 19 and 20 which, in relation with the incisive rod 16, provide very good stability in the upturned position of the device.

Figure 3:
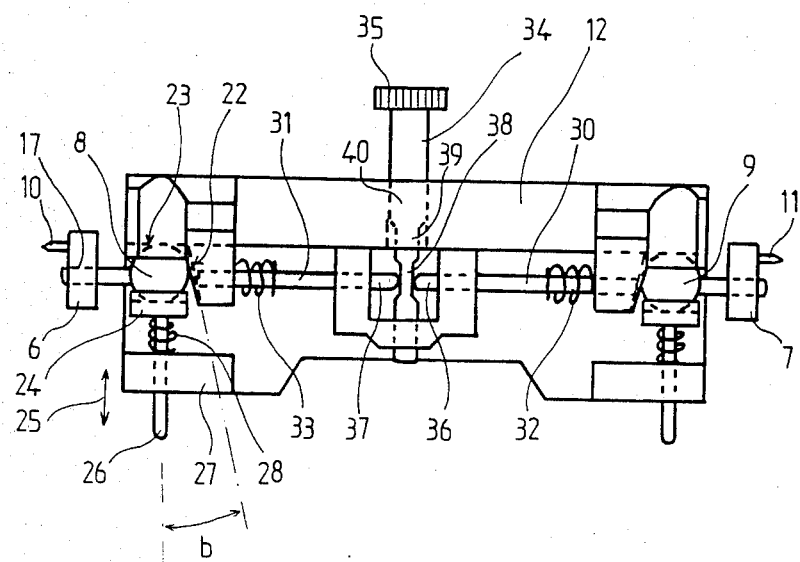
FIG. 3 shows a bottom view of an upper member hub in accordance with the present invention, the rods being in the closer position.
Figure 4:
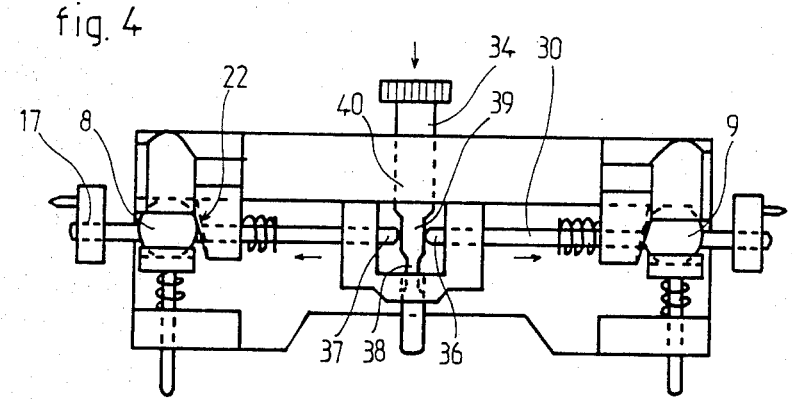
FIG. 4 shows the same hub with rods in the spaced apart position.

As shown in FIGS. 3 and 4, hub 12 comprises, in the vicinity of each of its ends, appropriate housings for housing the condylar balls. The two housings of the hub have a symmetrical arrangement with respect to the median axis of the device, it is therefore sufficient to describe one of the two housings. The housings are limited by a flat upper guide ramp 21, slanting towards the front by an angle a reproducing the condylar slope (FIG. 2). An outer lateral ramp 22, or BENNETT's wing, is open towards the front through an angle b reproducing BENNETT's angle. The housing is further limited by a rear wall 23 shaped so as to allow the transverse movements of the condylar balls.

For constructing an articulator which is easy to use, values of the condylar slope angles a and b and of BENNETT's angle are fixed. A condylar slope angle will for example be chosen close to 40°, and a BENNETT's angle close to 7°, so as to provide a device allowing most of the cases met with by the practitioner to be treated.

The housings are further limited towards the front by a front stop 24, mobile in translation with a front-rear movement parallel to the upper guide ramp 21 as shown by the double arrows 25. The front stop 24 is moveable between a first position in which it pushes the condylar ball back against the rear wall of the housing, and a second position in which it frees the condylar ball so as to allow it to move and more particularly to be introduced into and removed from the hub. Stop 24 is guided by a rod 26 passing through a front shoulder 27 in which it may be locked by a transverse screw 29. A spring 28 urges stop 24 rearwardly towards the rear wall 23.

The hub further comprises two independent rods 30 and 31, sliding transversely in the hub parallel to its axis, through guide bores.

In a first embodiment, shown in the Figures, rods 30 and 31 pass through corresponding bores provided in the fixed BENNETT wings such as wing 22. The rods are moveable between a closed up position, shown in FIG. 3, in which they release the condylar balls allowing the immediate lateral displacement of the upper member because the spacing between the condylar balls is greater than the spacing between the BENNETT wings. The rods may take up a spaced apart position shown in FIG. 4, in which they bear against the condylar balls so as to hold them without play in symmetrical position with respect to the longitudinal median plane of the upper member. Rods 30 and 31 are permanently urged inwardly by resilient means such as helical springs 32 and 33.

A control means 34 ensures movement of the rods. This means 34 comprises linear parts engaging in corresponding bores of the hub in which they slide freely, the action of the user being exerted on an end knob 35 accessible from the outside. The control means 34 is engaged between rods 30 and 31 and comprises external bearing faces against which the inner ends 36 and 37 of the rods come to bear under the action of springs 32 and 33. Thus, the control means 34 is a part providing spacing apart of the rods by a movement perpendicular to the axis of the rods.

In the embodiment shown in the Figures, the control means 34 comprise a reduced spacing zone 38. The rods are in the closed up position when this reduced spacing zone 38 is opposite their ends 36 and 37, as shown in FIG. 3. The means 34 also comprise a larger spacing zone 39 which, when it is engaged between the rods, pushes them back towards the condylar balls. A third even larger spacing zone 40, pushes the rods back to the maximum. Each of zones 38, 39 and 40 comprises a constant spacing and is connected to the following zone by a conical or wedge portion. A zone 38 will for example be chosen whose spacing allows the condylar balls to be completely released by rods 32 and 33 whose outer ends are then flush in the bore with the BENNETT wings 22. The spacing of zone 39 may be chosen greater by about 2.5 millimeters with respect to the spacing of zone 38 and zone 40 by a spacing greater than about 4 millimeters with respect to zone 38.

For effecting the adjustments, removable centering blocks 41 and 42 are used, shown in FIGS. 1 and 2. The removeable blocks 41 and 42 are adaptable respectively to the lower 3 and upper 13 platens and are shaped so as to fit one into the other as shown in the Figures. When they are fitted to the platens, the blocks hold the upper member 2 in a symmetrical position with respect to the plane of symmetry of the lower member 1, or centered position.

The operation of the device is as follows: let us assume that it is desired to adjust the articulator with an immediate lateral displacement of 1.25 millimeters. Blocks 41 and 42 are fitted to the corresponding platens, the shafts or the condylar balls are unlocked by means of screws 5, the control means 34 are engaged so as to dispose zone 39 between rods 32 and 33, the condylar balls are pushed back in abutment against the outer ends of the rods, and the shafts of the balls are locked by means of the locking screws 5. The articulator is then ready to operate: when the control means 34 is pressed in, inserting zone 39 between the rods, the upper member is held in a centered position by the rods bearing against the condylar balls. When the control means 34 are withdrawn, inserting the narrow zone 38 between the rods, the rods retract and the spacing between the condylar balls becomes greater than the spacing between the BENNETT wings 22, producing the immediate lateral displacement.

In another embodiment, control means 34 may be used such as a conical or wedge shaped part, having progressive spacing and pushing back the rods gradually during movement thereof. Means must then be provided for locking the control means 34, which locking means are not shown in the Figures.

In another embodiment, the BENNETT wings 22 are made moveable, allowing them to move translationally in a transverse direction, i.e. parallel to the axis of hub 12. The BENNETT wings 22 are firmly secured to each end of rods 32 and 33, so that movement of the control means 34 causes the BENNETT wings themselves to move away from or close to each other.

With the above described arrangements, in which the spacing between the condylar balls is adjustable, the same lower members may be used for forming articulators without immediate lateral displacement or with immediate lateral displacement. It is in fact sufficient to allow or prevent unlocking of screws 5. Furthermore, the locking screws 5 may be used for adjusting the spacing between the condylar balls in the factory, and thus reducing the tolerances required in machining the mechanical parts, the adjustment allowing variations to be taken up. The same locking screws allow complete articulators to be formed, with immediate lateral displacement, and so without requiring additional parts.

The present invention is not limited to the embodiments which have been explicitly described, but includes the different variations and generalisations thereof included within the scope of the following claims. Control means 34 of revolution may in particular be used, that is to say having a longitudinal shaft of revolution, sliding in corresponding cylindrical bores provided in the walls of the hub. The construction thereof is thus simpler, and a rotation of knob 35 has no effect on the spacing between the rods.

What is claimed is:

1. An articulator apparatus for the dental art, comprising a lower member whose front part forms a lower platen and supports an incisive plate, and whose rear part comprises two legs supporting two condylar balls forming ball joints on each of which is articulated a upper member comprising a rear hub having appropriate housings for housing the condylar balls, the upper member comprising an upper platen integral with the hub and whose front part receives an incisive rod bearing on the incisive plate, the housings of the hub being limited by a flat upper guide ramp slanting forwardly by an angle reproducing the condylar slope, by a lateral ramp and by a rear wall allowing the transverse movements of the condylar balls, the articulator further comprising means for selectively obtaining locking thereof in centered relation, wherein the centered relation locking is provided by means of two rods sliding transversely in the hub, moveable between a closed up position in which they release the condylar balls, allowing the immediate lateral displacement of the upper member due to the fact that the spacing between the condylar balls is greater than the spacing between the lateral ramps and a spaced apart position in which the rods bear without play against the condylar balls symmetrically with relation to the median longitudinal plane of the upper member, a control member for operating the rods and holding them in one or other position.

2. The articulator according to claim 1, wherein the control member comprises a spacing piece moveable perpendicularly to the axis of the rods by the user and being inserted between the two inner ends of the rods so as to urge them back towards the outside by its bearing faces, the bearing faces comprising a reduced spacing zone for leaving the rods in the closed up position when they are in abutment against this zone, and at least one larger spacing zone for holding the rods in the spaced apart position.

3. The articulator as claimed in claim 2, wherein the spacing piece is generally wedge shaped.

4. The articulator as claimed in claim 2, wherein said spacing piece comprises a first reduced and constant spacing zone, a second zone whose spacing is constant and greater than about 2.5 millimeters with respect to the first zone and a third zone whose spacing is constant and greater than about 4 millimeters with respect to the first zone, the zones being joined together by wedge shaped surfaces.

5. The articulator according to claim 2, wherein said rods are urged by resilient means tending to urge them close to one another.

6. The articulator as claimed in claim 2, wherein the control means is a piece of revolution sliding in guide bores formed in the walls of the hub.

7. The articulator as claimed in claim 1, wherein the outer ends of the rods are integral with the lateral ramps which are themselves moveable in translation in a transverse direction.

8. The articulator as claimed in claim 1, wherein said rods pass through a bore formed in the lateral ramps and come into abutment against the condylar balls.

9. The articulator as claimed in claim 8, further comprising means for adjusting the spacing of the condylar balls.

10. The articulator as claimed in claim 9, further comprising moveable centering blocks which may be fitted respectively to the lower platen and to the upper platen and which fit one in the other for holding the upper member in the centered position.

11. The articulator as claimed in claim 1 wherein the lateral ramp comprises a Bennett's wing.

12. The articulator as claimed in claim 7 wherein the lateral ramps comprise Bennett's wings.

13. The articulator as claimed in claim 8 wherein the lateral ramps comprise Bennett's wings.

* * * * *